United States Patent [19]
DeLuca et al.

[11] Patent Number: 5,880,292
[45] Date of Patent: Mar. 9, 1999

[54] ALL-TRANS-RETINOL METABOLITE

[75] Inventors: Hector F. DeLuca, Deerfield; Heinrich K. Schnoes, Madison, both of Wis.; Rafal R. Sicinski, Warsaw, Poland; Xiujuan Jia, Madison, Wis.

[73] Assignee: Wisconsin Alumni Research Foundation, Madison, Wis.

[21] Appl. No.: 927,511

[22] Filed: Sep. 11, 1997

[51] Int. Cl.$^6$ .......................... C07D 333/10; A61K 31/38
[52] U.S. Cl. ................... 549/78; 549/29; 549/78; 514/438
[58] Field of Search ................ 549/78; 514/438

[56] References Cited

U.S. PATENT DOCUMENTS

| | | | |
|---|---|---|---|
| 4,190,594 | 2/1980 | Gander et al. | 260/404 |
| 4,459,404 | 7/1984 | Frickel et al. | 548/253 |
| 4,568,757 | 2/1986 | Carroll et al. | 549/294 |
| 4,757,140 | 7/1988 | DeLuca et al. | 536/27 |

OTHER PUBLICATIONS

Retinal, The Merck Index, 1989, pp. 1298–1299, No. 8165.
Vitamin A, The Merck Index, 1989, pp. 1576, No. 9918.
Retinoic Acid, The Merck Index, 1989, pp. 1298–1299, No. 8167.

*Primary Examiner*—Jose'G. Dees
*Assistant Examiner*—Sabiha N. Qazi
*Attorney, Agent, or Firm*—Andrus, Sceales, Starke & Sawall

[57] ABSTRACT

In vitro incubation of all-trans-retinol (atROL) with kidney homogenate from vitamin A deficient and retinoic acid supplemented (VAD-RAS) female rats produced a new retinol metabolite. The metabolite has the structure

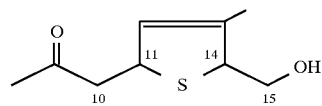

and is believed useful for the treatment of skin disorders such as acne, psoriasis, and ultraviolet light skin damage, as well as for promoting female fertility and the maintenance of pregnancy.

2 Claims, 9 Drawing Sheets

ALL-TRANS-RETINOL METABOLITE

STATEMENT REGARDING FEDERALLY SPONSORED RESEARCH OR DEVELOPMENT

This invention was made with United States government support awarded by the following agencies:
NIH Grant No.: DK14881
The United States has certain rights in this invention.

BACKGROUND OF THE INVENTION

The present invention relates to a metabolite of all-trans-retinol, and more particularly to such a metabolite possessing a thiophene ring.

Retinol and its metabolites participate in many physiological processes, such as growth and development, reproduction, cellular differentiation and proliferation, and vision. Except in the visual system where the functional forms of a vitamin A have been well characterized (Wald, Science 162, 230–239, 1968), other biological functions of vitamin A are thought to be mediated by the action of retinoic acids (RAs) which interact with retinoic acid receptor (RAR) and retinoic acid X receptor (RXR) heterodimers or RXR homodimers and, therefore, regulate gene expression (Allenby et al, Proc. Natl. Acad. Sci. USA 90, 30–34, 1993; Nagpal et al, EMBO J. 12, 2349–2360, 1993). The discovery of RARs (Petkovich et al, Nature (London) 330, 444–450, 1987; Brand et al, Nature (London) 332, 850–353, 1988; Giguere et al, Nature (London) 330, 624–629, 1987; Benbrook et al, Nature, 333, 669–672, 1988; Krust et al, Proc. Natl. Acad. Sci. USA 86, 5310–5314, 1989; Zelent et al, Nature (London) 339, 714–717, 1989) and RXRs (Mangelsdorf et al, Nature (London) 345, 224–229, 1990; Mangelsdorf et al, Genes Dev. 6, 329–344 1992; Yu et al, Cell 67, 1251–1266, 1991) leads people to understand the mechanisms of RA action on the molecular level.

However, overwhelming data demonstrate that rats fed retinol free and all-trans-retinoic acid (atRA) supplemented diet fail to reproduce (Thompson et al, Proc. R. Soc. Lond B. Biol. Sci., 159, 510–535, 1964; Takahashi et al, J. Nutr. 105, 1299–1310, 1975; Wellik and DeLuca, Biol. Rep. 53, 1392–1397, 1995; Wellik et al, Am. J. Physiol. 292 (Endocrinol. Metab. 35), E25–E29, 1997). Although vitamin A-deficient, atRA supplemented (VAD-RAS) female rats can become pregnant after mating with healthy males, they invariably resorb their fetuses at approximately day 15 of gestation. Work by Wellik and DeLuca, Biol. Rep. 53, 1392–1397, 1995, showed that retinol is required no later than day 10 of gestation in order to prevent fatal resorption in the VAD-RAS female rats, and administration of a dose as little as 2 µg on day 10 of gestation could prevent the resorption and allow parturition to complete.

Wellik and DeLuca, Arch. Biochem. Biophys. 330, 355–362, 1996 studied atROL metabolites in day 10 conceptuses of VAD-RAS rats. After administration of a dose of 2 µg atROL into the 10-day pregnant female rats, an unknown metabolite was found in the conceptuses. The concentration of this metabolite increases through 6 hour post-dose. It did not react with phosphatase, glucuronidase or sulfatase, therefore, it was unlikely to be an excretion product. Further study showed that the metabolite was also found in several other tissues collected from the VAD-RAS female rats. Kidneys from the VAD-RAS female rats contained 70 times the amount of the metabolite found in the conceptuses. However, the small quantity of the metabolite produced in vivo was not sufficient for determination of the structure of the compound.

Based on the previous data by Wellik and DeLuca, Arch. Biochem. Biophys. 330, 355–362, 1996, the present study was focused on establishing an in vitro generation method which would obtain the unknown atROL metabolite in quantities required for its structural identification. The structure of this unknown metabolite was studied by ultraviolet (UV), infrared (FT-IR) and nuclear magnetic resonance ($^1$H NMR) spectroscopy as well as mass spectrometry.

BRIEF SUMMARY OF THE INVENTION

A metabolite of all-trans-retinol possessing a thiophene ring. The metabolite is characterized by the formula:

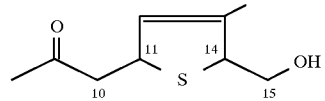

where carbons 11 and 14 are both asymmetric centers thus enabling the metabolite to exist in four distinct isomeric forms.

The new retinol metabolite was produced via in vitro incubation of all-trans-retinol (atROL) with kidney homogenate from vitamin A deficient and retinoic acid supplemented (VAD-RAS) female rats. Spectroscopic studies of the metabolite showed that it is a nine-carbon fragment which resulted from an oxidative cleavage of the atROL's side chain. The cleavage occurred at C-9, which was then oxidized to a keto group. The primary hydroxy group from atROL was preserved in the metabolite. A sulfide bridge was formed between C-11 and C-14, which interrupted the double bond conjugation. The formation of the new metabolite, possessing a 2,5-dihydrothiophene ring, is catalyzed by the enzyme(s) located in the cytosolic fraction of the kidneys cells.

It is believed this metabolite will provide a therapeutic agent for the treatment of alopecia and skin disorders such as acne, ichthyosis, psoriasis, dry skin (lack of dermal hydration), undue skin slackness (insufficient skin firmness), insufficient sebum secretion, wrinkles, or actinic ultraviolet (UV) light skin damage. The metabolite may also be useful as an anti-cancer agent, especially against leukemia, colon cancer, breast cancer and prostate cancer. This metabolite may also find use in promoting female fertility and in maintaining pregnancy.

The treatment may be topical, transdermal, oral or parenteral in dosages of from about 0.01 µg/day to about 100 µg/day with 0.1 µg/day to 50 µg/day preferred. The compounds may be present in a composition in an amount of from about 0.01 µg/gm to about 100 µg/gm of the composition with 0.1 µg/gm to 50 µg/gm of composition preferred.

BRIEF DESCRIPTION OF THE SEVERAL VIEWS OF THE DRAWING

FIG. 5 is a graph illustrating GC-MS analysis of metabolite Xa wherein

DETAILED DESCRIPTION OF THE INVENTION

Figure 1:
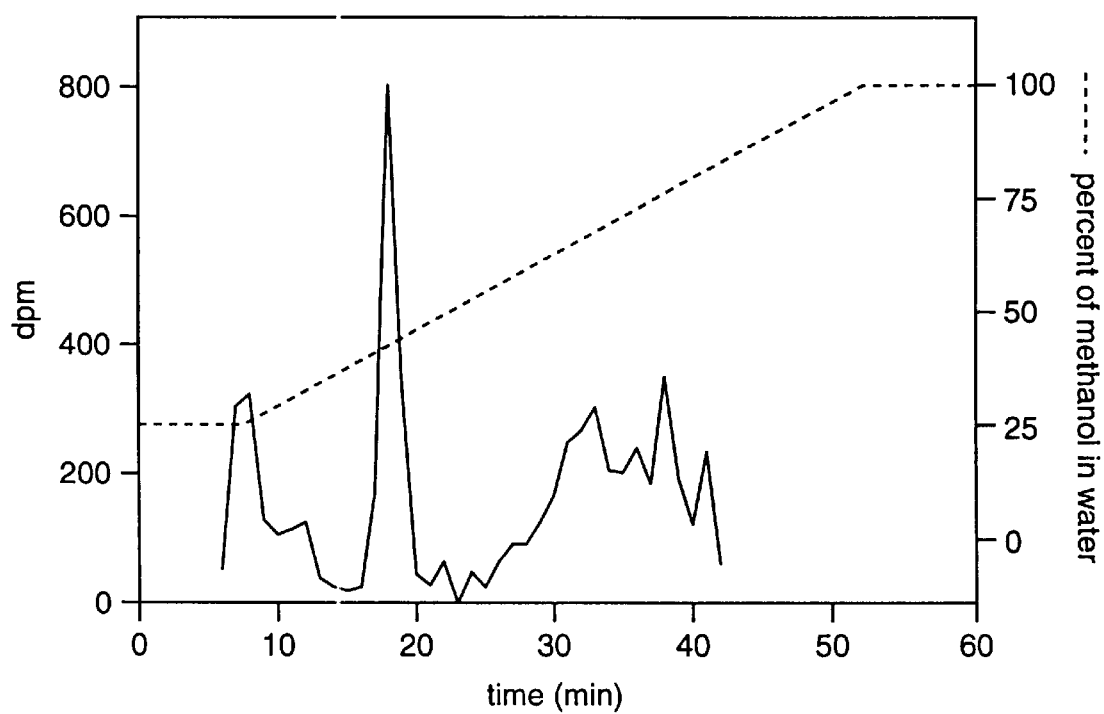
FIG. 1 is a graph illustrating radioactivity profiles of the aqueous/ethanol fraction extracted from in vitro incubation of VAD-RAS rat kidney homogenate in 100 mM Tris buffer (ph 7.4) at 37° C. for 15 min.

A metabolite of all-trans-retinol has now been found and identified as 2-hydroxymethyl-3-methyl-5-(2'-oxopropyl)-2,5-dihydrothiophene. The metabolite is characterized by the formula:

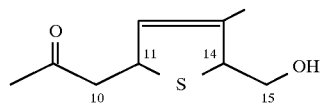

where carbons 11 and 14 are both asymmetric centers enabling the metabolite to exist in four distinct isomer forms. It should be noted that the numbering system applied for retinoids is used throughout this specification and claims.

The preparation, isolation and identification of the metabolite can be accomplished as follows.

Chemicals and solvents. [11,12-$^3$H]atROL and [15-$^3$H] atROL were purchased from DuPont (New England Nuclear, Boston, Mass.), [20-$^3$H]atROL was a gift from DuPont. atROL was purchased from Fluka Biochemika (Switzerland). The solvents and reagents were obtained from the following sources: pyridine and TBT (a combination of TMS-imidazole, bis-TMS-acetamide and trimethylchlorosilane) from Pierce (Rockford, Ill.), acetic anhydride from Fisher (Pittsburgh, Pa.), chloroform-d and acetone-d$_6$ (100 atom % D) from Aldrich (Milwaukee, Wis.). Sucrose, Trizma hydrochloride and other chemicals were purchased from Sigma (St. Louis, Mo.). Water of HPLC grade was purchased from Fisher (Pittsburgh, Pa.). All other solvents were B&J Brand high purity HPLC grade solvents (Baxter, Stone Mountain, Ga.).

Animals. Female Harlan-Sprague-Dawley rats were obtained at weaning and fed a vitamin A free synthetic, purified diet (Suda et al, J. Nutr. 100, 1049–1052, 1970) modified as described in Wellick and DeLuca Biol. Rep., 53, 1392–1397 (1995) until they reach vitamin A deficiency which was inferred by weight loss. Then, the animals were given the same diet with supplementation of all-trans-retinoic acid (atRA) at a concentration of 5 mg/kg diet.

In vivo generation of the unknown retinol metabolite. The in vivo production of the unknown retinol metabolite from the VAD-RAS female rats was conducted following the procedure used by Wellik and DeLuca, Arch. Biochem. Biophys. 330, 355–362, 1996, except that kidneys instead of conceptuses were collected and extracted.

In vitro generation of the unknown retinol metabolite. The female VAD-RAS rats were anesthetized with diethyl ether and kidneys were removed, cleaned and homogenized in 5 volumes of 0.25M sucrose/100 mM Tris buffer solution (pH 7.4) at 0° C. An aliquot of 0.5 ml of the homogenate was mixed with 2.5 ml of 100 mM Tris buffer (pH 7.4) in 25 mL erlenmeyer flask. An aliquot of 10 μl of $^3$H-labeled ([11, 12-$^3$H] or [15-$^3$H] or [20-$^3$H]) all-trans-retinol ethanolic solution with a concentration of 7.0 mM and specific activity of 14.0 mCi/mmol was added to each flask. The flasks were placed on a shaker in 37° C. water bath. They were incubated for different period of time (from 0 to 60 min), then removed from the water bath, and the metabolite was extracted as stated below.

Subcellular fractionation. Subcellular fractions of the kidney homogenate were separated by following the method by Burgos-Trinidad, et al (1986). The kidney homogenate was centrifuged at 500 g for 10 min to separate nuclei (N) and debris from cytosol (C) and mitochondria (M). The supernatants were centrifuged at 10000 g for 10 min to separate the mitochondria from the cytosol. The nuclei and mitochondria fractions were washed twice with 0.25M sucrose/100 mM Tris buffer solution (pH 7.4). Each of these subcellular fractions was tested for the in vitro generation of this unknown retinol metabolite by following the same procedure stated above. To avoid isomerization of retinoids all experiments were conducted under yellow light or shielded from white light.

Extraction and HPLC purification of the unknown metabolite. The extraction procedure was similar to that used by Wellik and DeLuca, Arch. Biochem, Biophys. 330, 355–362, 1996. One volume of 0.01% ethanolic solution of 2,6-di-tert-butyl-p-cresol (BHT) and 0.5 volume of 4.25M NaCl in 0.015% of n-propylgallate aqueous solution were added to the incubation mixture. This aqueous mixture was extracted twice with one volume of hexane to remove retinol esters, retinol and other non polar compounds. The aqueous solution was evaporated to dryness in vacuo, and the dry residue was extracted with methylene chloride. The methylene chloride solution was then evaporated in vacuo. The residue was redissolved in reverse-phase HPLC solvent and stored under argon at −20° C. for future HPLC analyses.

The Waters Photo Diode Array (PDA) HPLC equipment (Waters Corporation, Milford, Mass.) was used for both reverse-phase (RP) and normal-phase (NP) chromatography. The instrument includes 600E Pump, $^{717}$plus Autosampler, 717 Temperature Controller, 996 PDA Detector and Waters Fraction Collector. The data were acquired and processed by Millennium v2.15 PDA software. A Phenomenex Zorbax-ODS column (4.6 mm×25 cm; Terrance, Calif.) was used for RP-HPLC analysis and an All-tech CN-AQ 5μ column (4.6 mm×25 cm; Deerfield, Ill.) was used for NP-HPLC analysis. The RP-HPLC solvent system was a gradient of methanol in water and the NP-HPLC solvent systems were a gradient of isopropanol (IPA) in methylene chloride/hexane. The exact gradients used are shown in the figures.

Derivatization procedures. Acetylation of metabolite was performed by treating a sample with acetic anhydride/pyridine solution (1:2, 30 μL) at room temperature overnight. The reaction solution was then evaporated twice with one volume of hexane to ensure the removal of solvents. The residue was redissolved in NP-HPLC mobile phase for NP-HPLC purification. Trimethylsilylation was performed by reaction of a sample with TBT (4 $\mu$l) in pyridine (4 $\mu$l) for 60 min at room temperature. An aliquot of the reaction mixture was directly analyzed by gas chromatograph-mass spectrometer (GC-MS, described below). All reactions were conducted under argon atmosphere.

Spectroscopic methods. Ultraviolet (UV) spectra were recorded by PDA Detector and the corresponding absorption maxima obtained from the Millennium Spectrum Review Reports generated by Millennium v2.15 software. Infrared (IR) spectra were recorded on an ATI Mattson Infinity Series, 60AR FT-IR spectrometer (Madison, Wis.) in KBr pellets. $^1$H nuclear magnetic resonance (NMR) spectra were measured at 500 MHz with a Bruker DMX-500 spectrometer in the solvent noted. A Finnigan Magnum (San Jose, Calif.) GC-MS was used for low resolution GCMS measurements. A J & W DB-5MS capillary column (0.25 mm i.d.×30 m) was coupled directly to the ion source. Helium was used as carrier gas at 15 psi. The split/splitless injector was used in the splitless mode at 280° C. The GC oven temperature as programmed as follows: initial temperature 40° C.; held at 40° C. for 5 min. The transfer line and trap manifold were at 320° C. and 150° C., respectively. The ion trap was operated in the EI mode under auto gain. High resolution electron impact mass spectra were recorded at 70 eV on a Kratos DS-50 TC instrument equipped with a Kratos DS-55 data acquisition system.

Results

Incubation of $^3$H-labeled atROL with VAD-RAS rat kidney homogenate in Tris buffer solution (pH 7.4) was carried out for 15 min, and the aqueous extract of the incubation mixture was analyzed on RP-HPLC. In vitro incubation produced a peak with radioactivity (FIG. 1) comigrating with the unknown atROL metabolite found from the VAD-RAS rat kidneys after 4 hr oral administration of atROL (not shown).

Figure 2:
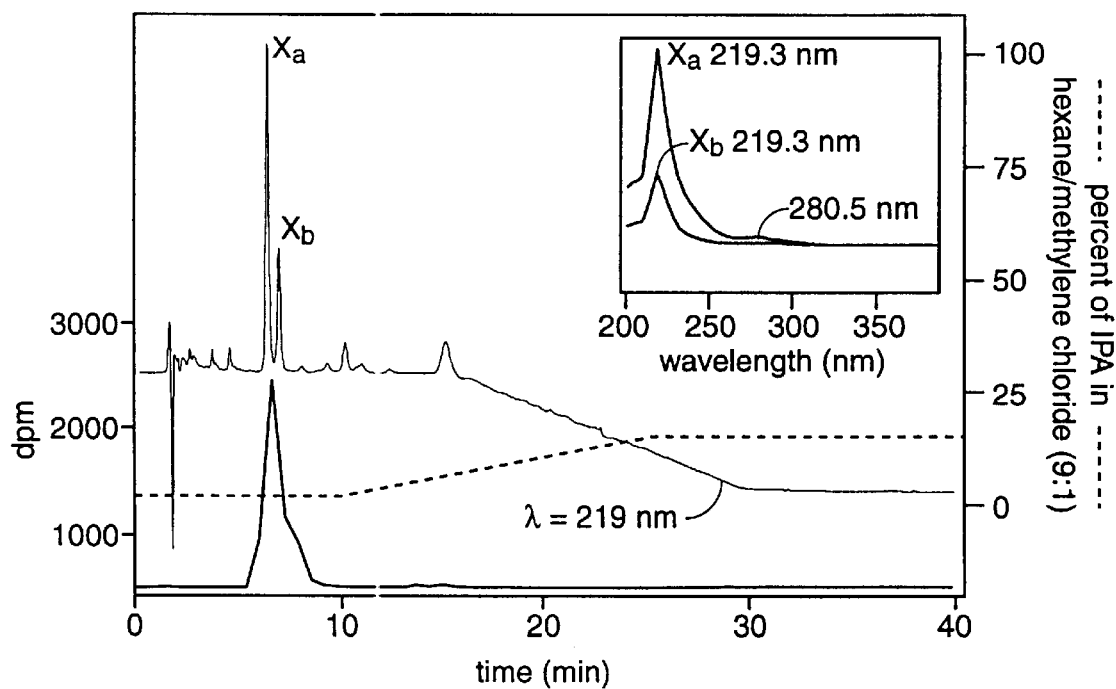
FIG. 2 is a graph illustrating NP-HPLC purification of the metabolite peak collected off RP-HPLC column showed the radiolabeled compounds comigrated with two UV peaks that have the same UV profile as shown in the insert; the dotted line represents HPLC solvent gradient condition.
Figure 3:
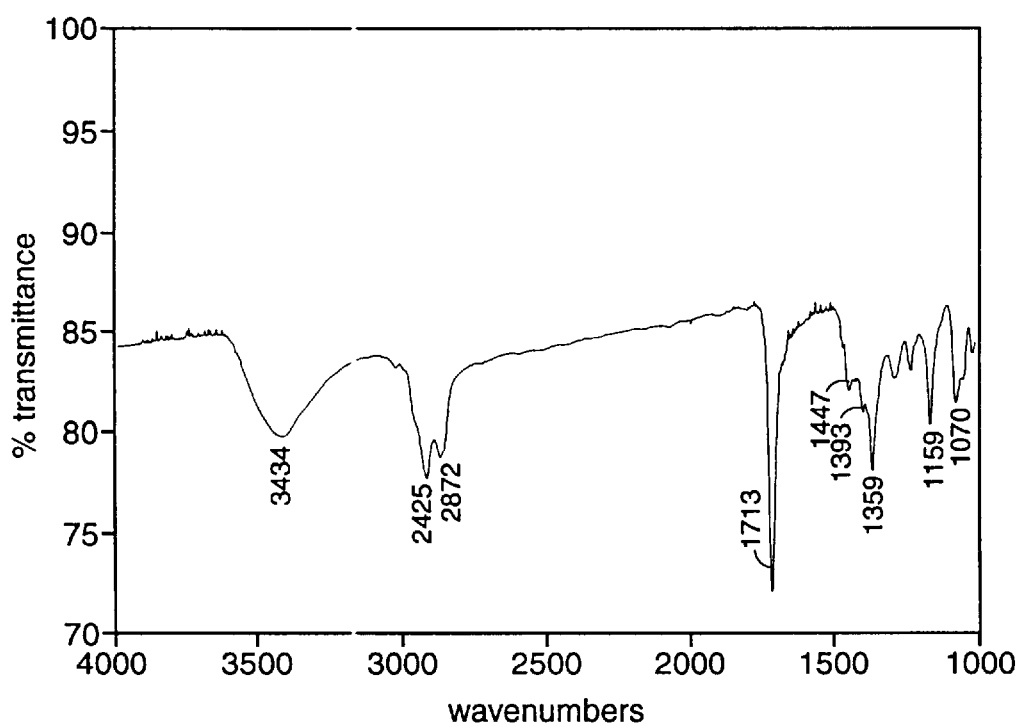
FIG. 3 is a graph illustrating FT-IR spectrum of Xa in KBr pellet.
Figure 4:
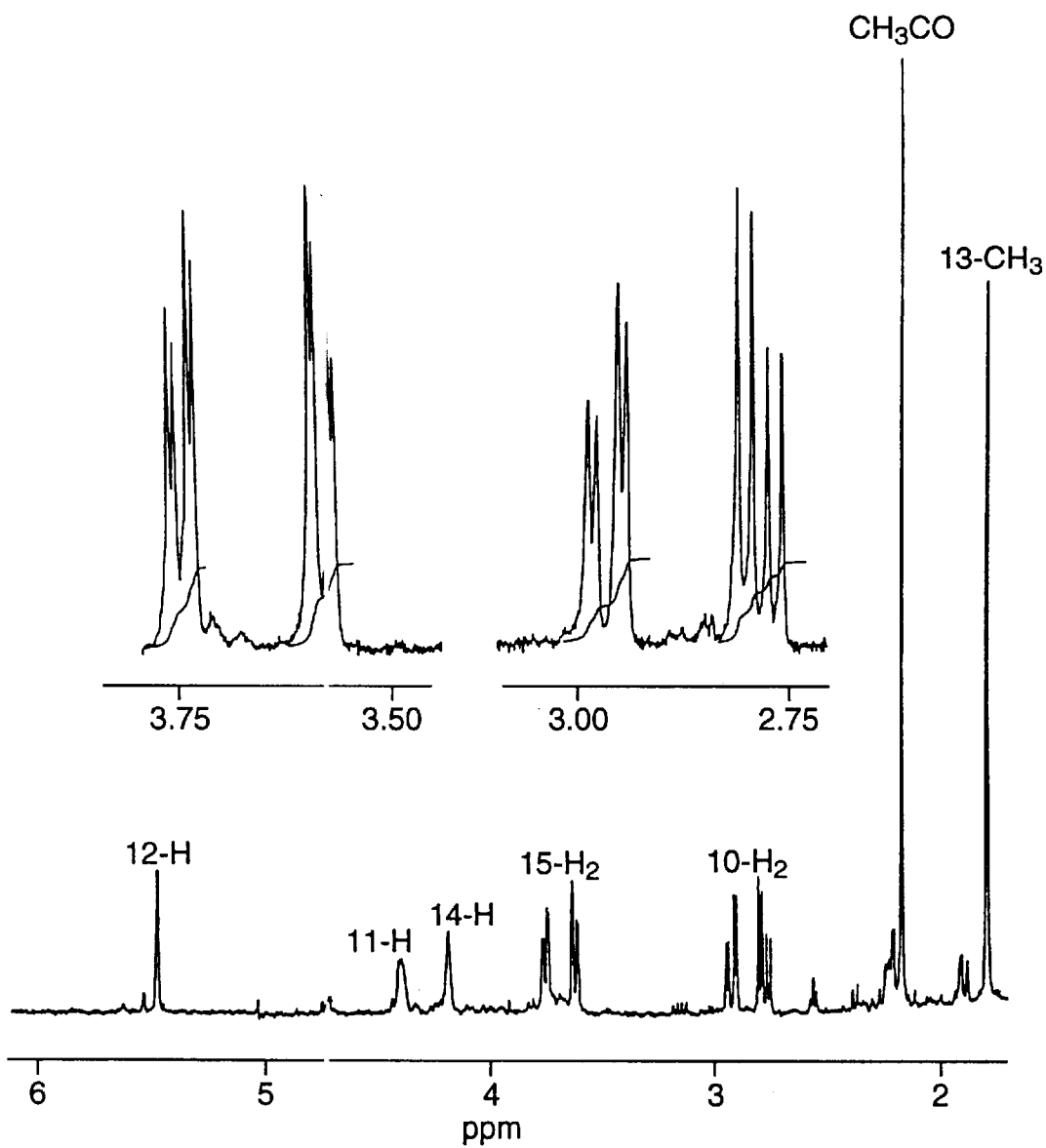
FIG. 4 is a graph illustrating $^1$H NMR spectrum of Xa in chloroform-d (100 atom % D) at 4° C.
Figure 5A:
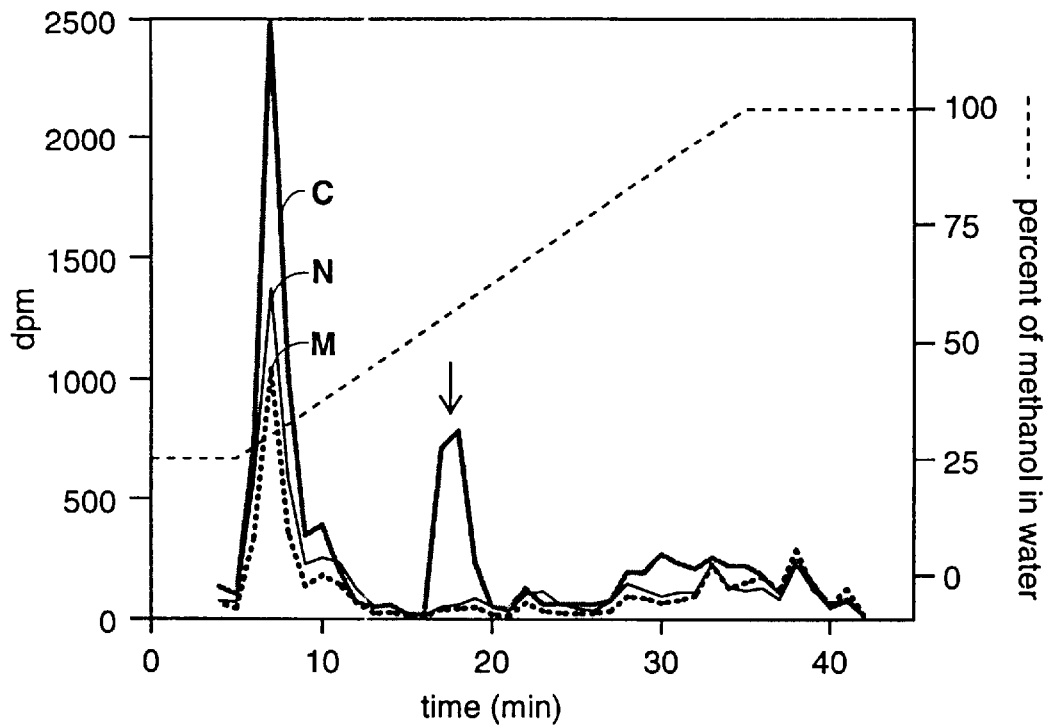
FIG. 5(a) illustrates GC purification of Xa.
Figure 5B:
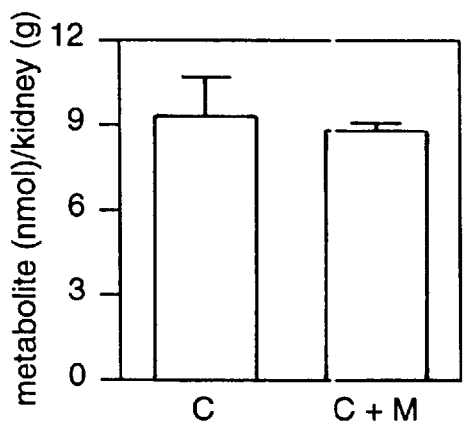
FIG. 5(b) illustrates MS spectrum of the Xa peak purified by GC.

Further purification of this peak on NP-HPLC system with a gradient of isopropanol (IPA) in methylene chloride/hexane (1:9) solvent system allowed further separation of the metabolite into two radioactive peaks (FIG. 2). In vitro incubation produced a large amount of the first peak (Xa, retention time 6.4 min) and a much smaller amount of the second peak (Xb, retention time 7.0 min). Calculation based on radioactivity gave about a 4 to 1 ratio of Xa to Xb. The spectral properties of the isolated compounds are as follows: Xa: UV (Insert of FIG. 2) $\lambda_{max}$ 219.3, 280.5 nm, A219/A280>30; IR (FIG. 3) 3434 (OH), 2925, 2872, 1713 (C=O), 1447, 1393, 1359, 1159, 1070 (C-O) cm$^{-1}$; $^1$H NMR (CDCl$_3$) (FIG. 4) $\delta$ 1.788 (3H, br s, 13-CH$_3$), 2.17 (3H, s, CH$_3$CO), 2.77 (1H, dd, J=17.9, 8.4 Hz, one of 10-H$_2$), 2.92 (1H, dd, J=17.9, 5.5 Hz, one of 10-H$_2$), 3.62 (1H, dd, J=11.6, 2.9 Hz, one of 15-H$_2$), 3.75 (1H, dd, J=11.6, 3.7 Hz, one of 15-H$_2$), 4.19 (1H, m, 14-H), 4.40 (1H, m, 11-H), 5.48 (1H, br s, 12-H): $^1$H NMR (CD$_3$COCD$_3$) $\delta$ 1.798 (3H, br s, 13-CH$_3$), 2.10 (3H, s, CH$_3$CO), 2.95 (1H, dd, J=17.8, 4.8 Hz, one of 10-H$_2$; the other 10-H overlapped with water peak at 2.85 ppm), 3.60–3.70 (3H, br m, CH$_2$OH), 4.02 (1H, m, 14-H), 4.26 (1H, m, 11-H), 5.47 (1H, br s, 12-H); GCMS (FIG. 5) (rel intensity) 186 (M$^+$, 1), 168 (M$^+$-H$_2$O, 6), 156 (M$^+$-CH$_2$O, 29), 155 (M$^+$-CH$_2$OH, 40), 113, (M$^+$-CH$_2$O-CH$_3$CO, 100), 111 (20), 43 (CH$_3$CO$^+$, 42); exact mass calcd for: C$_9$H$_{14}$O$_2$S 186.0714, found 186.0713, C$_9$H$_{12}$OS 168.0609, found 168.0608, C$_8$H$_{12}$OS 156.0609, found 156.0621, C$_8$H$_{11}$OS 155.0531, found 155.0548, C$_6$H$_9$OS 113.0425, found 113.0431;

Xb: UV $\lambda_{max}$ 219.3, 280.5 nm, A219/A280>30; $^1$H NMR (CDCl$_3$) $\delta$ 1.783 (3H, br s, 13-CH$_3$), 2.18 (3H, s, CH$_3$CO), 2.77 (1H, dd, J=18.1, 9.3 Hz, one of 10-H$_2$), 2.95 (1H, dd, J=18.1, 4.9 Hz, one of 10-H$_2$), 3.64 (1H, dd, J=11.7, 2.8 Hz, one of 15-H$_2$), 3.78 (1H, dd, J=11.7, 3.7 Hz, one of 15-H$_2$), 4.20 (1H, m, 14-H), 4.46 (1H, m, 1-H), 5.45 (1H, br s, 12-H); GCMS (rel intensity) 186 (M$^+$, 2), 168 (M$^+$-H$_2$O, 7), 156 (M$^+$-CH$_2$O, 36), 155 (M$^+$-CH$_2$OH, 35), 113 (M$^+$-CH$_2$O-CH$_3$CO, 100), 111 (24), 43 (CH$_3$CO$^+$, 42); exact mass calcd for C$_9$H$_{14}$O$_2$S 186.0714, found 186.0713.

Figure 6A:
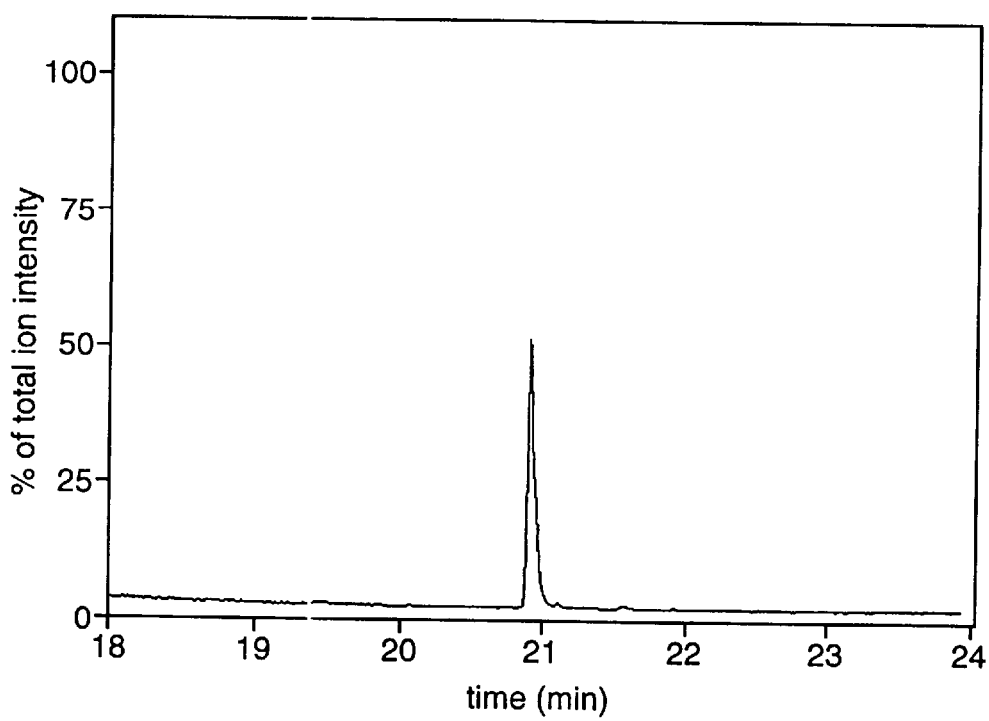
FIG. 6 is a graph illustrating in vitro production of the metabolite by each of the subcellular fractions of the VAD-RAS kidney homogenate 15 min after incubation with $^3$H-labeled atROL at 37° C. with FIG. 6(a) illustrating radiolabel elution of the aqueous/ethanol fraction extracted from each of the subcellular fractions which showed the metabolite was produced only by the cytosolic fraction.
FIG. 6(b) illustrating a comparison of the amount of the metabolite produced by the C fraction and the C+M fraction; the dotted line in FIG. 6(a) represents the RP-HPLC solvent gradient condition; and the arrow in FIG. 6(a) indicates the metabolite peak.
Figure 6B:
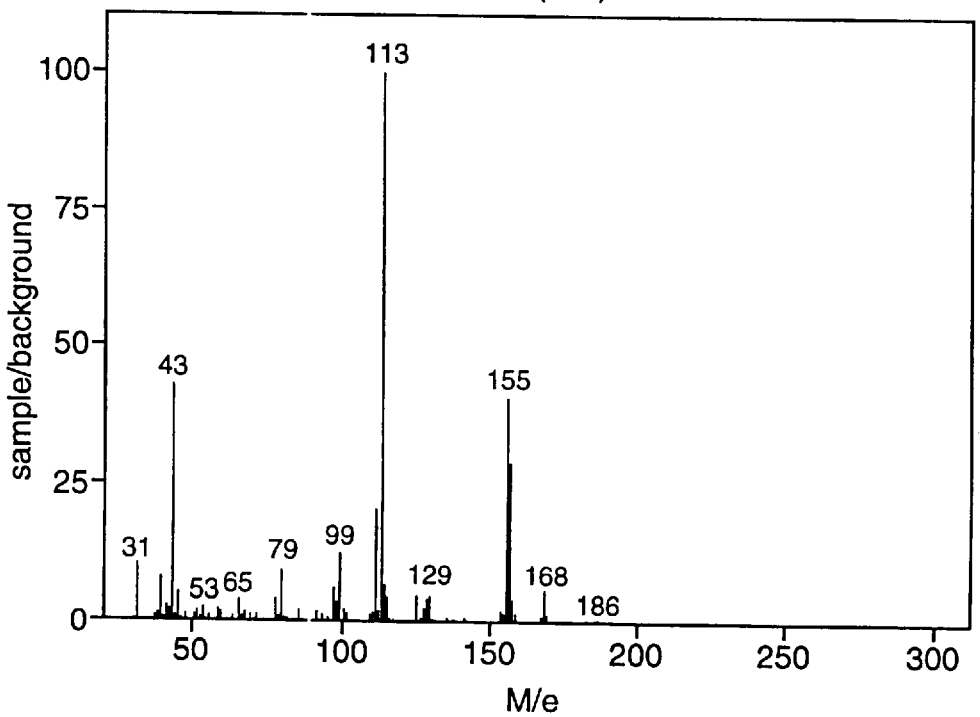

Incubation of 20- $^3$H-labeled atROL with each of the subcellular fractions of the VAD-RAS kidney homogenate at 37° C. for 15 min showed the unknown metabolite was produced only by the C fraction (FIG. 6a). Incubation of the $^3$H-labeled atROL with the combination of C and M (C+M) fractions at 37° C. for 15 min produced the same amount of the metabolite as that with only the C fraction (FIG. 6b). Thereafter, to simplify the in vitro generation procedure, the C+M fraction, instead the C fraction, was used for the in vitro generation for the metabolite in the following experiments.

Figure 7:
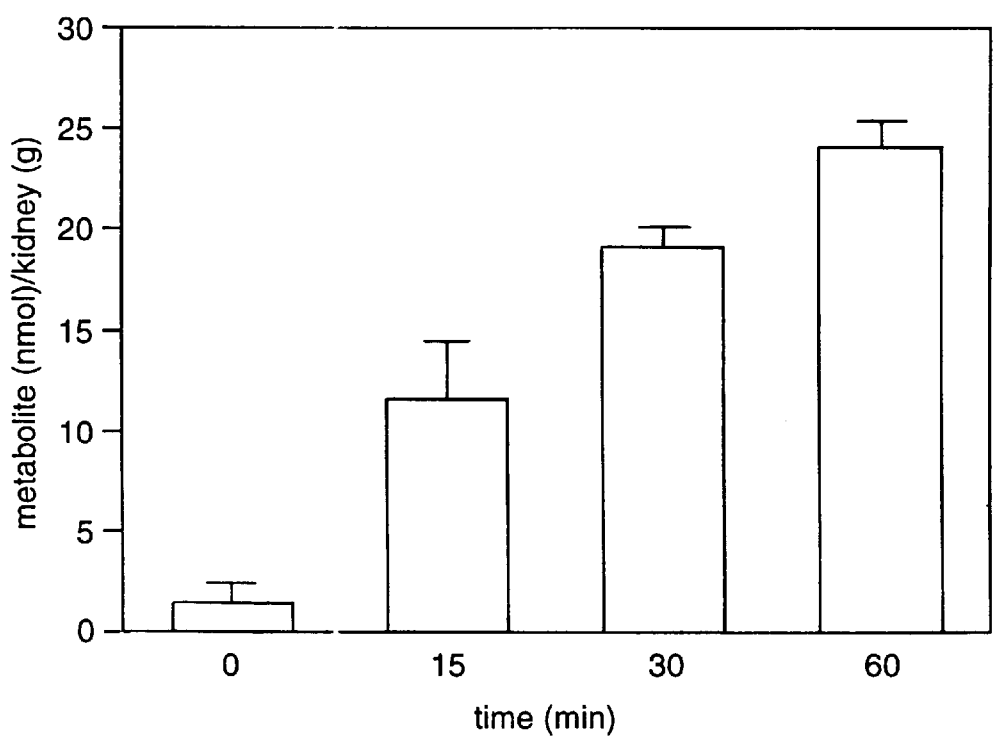
FIG. 7 is a graph illustrating the amount of the metabolites (Xa+Xb) produced by the C+M fraction after different time of incubation with (20-$^3$H) atROL at 37° C.
Figure 8:
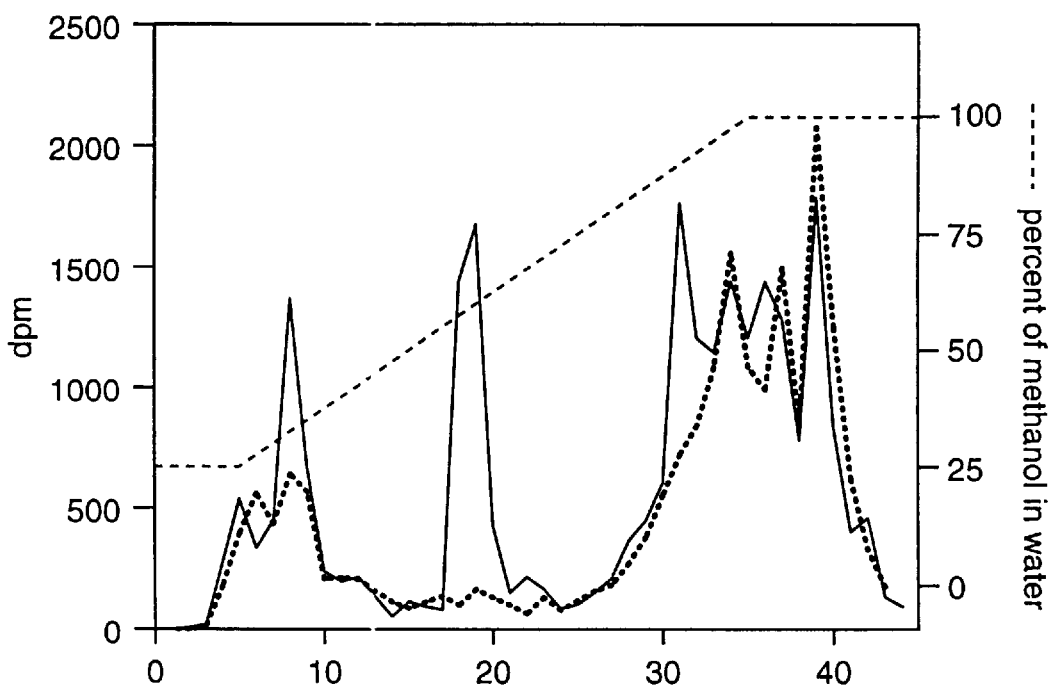
FIG. 8 is a graph illustrating RP-HPLC purification of the aqueous/ethanol fraction extracted from the sample (solid line) and the 60 min control (dotted line) illustrating the absence of the metabolite peak in the control.

A time course experiment showed the amount of the metabolite produced by the C+M fraction of the VAD-RAS kidney homogenate increased with time and 60 min incubation produced the highest amount of the metabolite (FIG. 7). In order to exclude the possibility that the metabolite was produced, in vitro, by some random degradation, the hot [20-$^3$H] atROL was incubated in 2.5 mL 100 mM Tris buffer (pH 7.4) and 0.5 mL 0.25M sucrose/100 mM Tris buffer solution (pH 7.4) (control), or 2.5 mL 100 mM Tris buffer (pH 7.4) and 0.5 mL the C+M fraction of the VAD-RAS rat kidney homogenate (sample), at 37° C. for 60 min. RP-HPLC analysis of the aqueous/ethanol fraction of the 60 min control and sample showed an absence of the metabolite peak from the control (FIG. 8).

Figure 9:
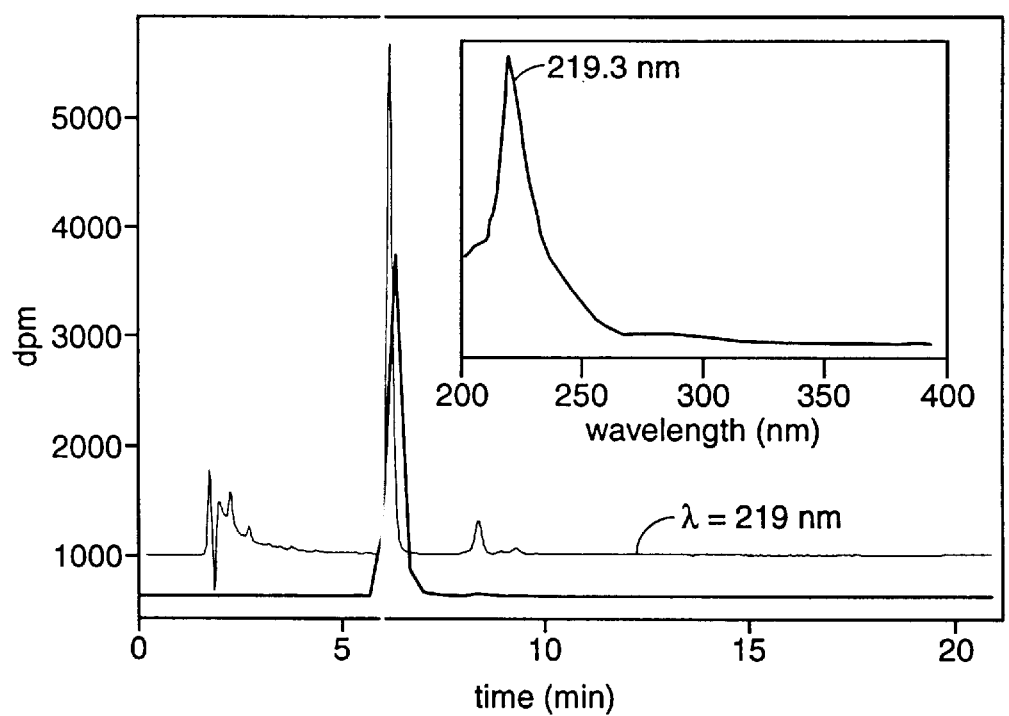
FIG. 9 is a graph illustrating NP-HPLC purification of the acetylated metabolite Xa utilizing a methylene chloride/IPA/hexane (10:0.5:89.5) isocractic solvent system; the insert shows the UV spectrum of the acetylated compound.

The acetylated Xa was purified on NP-HPLC using methylene chloride/IPA/hexane (10:0.5:89.5) isocratic solvent system. It was eluted at about 6 min (FIG. 9). Spectral properties of acylated derivative are as follows: UV (Insert of FIG. 9) $\lambda_{max}$ 219.3, 280.5 nm, A219/A280>30; $^1$H NMR (CDCl$_3$) $\delta$ 1.790 (3H, br s, 13-CH$_3$), 2.10 (3H, s, AcO), 2.17 (3H, s, CH$_3$CO), 2.78 (1H, dd, J=18.1, 9.2 Hz, one of 10-H$_2$), 2.90 (1H, dd, J=18.1, 5.4 Hz, one of 10-H$_2$), 4.09 (1H, dd, J=11.3, 7.4 Hz, one of 15-H$_2$), 4.15 (1H, m, w/2=15 Hz, 14-H), 4.30 (1H, dd, J=11.3, 4.6 Hz, one of 15-H$_2$), 4.37 (1H, m, w/2=19 Hz, 11-H), 5.49 (1H, br s, 12-H); GCMS (rel intensity) 228 (M$^+$, 1), 168 (M$^+$ -AcOH, 37), 155 (M$^+$ -CH$_2$OAc, 13), 125 (M$^+$ -AcOH-CH$_3$CO, 16), 113 (40), 111 (39), 43 (CH$_3$CO$^+$, 100); exact mass calcd for: C$_{11}$H$_{16}$O$_3$S 228.0820, found 228.0817, C$_9$H$_{12}$OS 168.0609, found 168.0607, C$_8$H$_{11}$OS 155.0531, found 155.0526, C$_7$H$_9$S 125.0425, found 125.0425.

The silylated Xa was purified by GC and analyzed by MS (GC-MS conditions described in Materials and Methods) and exhibits the following mass spectrum: GCMS (rel intensity) 258 (M$^+$, 2), 168 (M$^+$ -Me$_3$SiOH, 43), 155 (M$^+$ -CH$_2$OSiMe$_3$, 35), 113 (100), 111 (34), 103 (21), 73 (23), 43 (CH$_3$CO$^+$, 34).

Discussion all-trans-Retinoic acid is able to support early fetal development, but itself is not sufficient to allow successful gestation in vitamin A deficient rats (Thompson et al Proc. R. Soc. Lond. B. Biol. Sci. 159, 510–535, 1964; Takahashi et al, J. Nutr. 105, 1299–1310, 1975; Wellik and DeLuca, Biol. Rep. 53, 1392–1397, 1995; Wellik, et al, Am. J. Physiol, 272 (Endocrinol. Metab. 35), E25–E29, 1997). The mechanism by which retinol is absolutely required for a successful gestation to complete is not known. Previously, Wellik and DeLuca, Arch. Biochem. Biophys. 330, 355–362, 1996) found a new, early appearance polar retinol metabolite in the kidneys and 10-day old conceptus after oral administration of 2 μg atROL to the VAD-RAS mother.

In this study, in vitro incubation of atROL with the kidney homogenate of the VAD-RAS rat produced a metabolite which coeluted with the unknown metabolite reported by Wellik and DeLuca, Arch. Biochem. Biophys. 330, 355–362, 1996 on the RP-HPLC system. The metabolite peak was absent from the 0 min incubation and 60 min control. Therefore, the metabolite was produced by the kidney cells. NP-HPLC purification of the metabolite peak collected off RP-HPLC column separated the radioactive materials into two peaks, Xa and Xb. In vitro incubation predominantly produced metabolite Xa with a small quantity of Xb.

Both retinol metabolites Xa and Xb, isolated in this study, absorb UV light; however, their absorption maxima differ drastically from those observed for retinoids. They both exhibited a strong peak at 219.3 nm suggesting the absence of double bond conjugation. GC-MS analyses of the two metabolites provided low resolution spectra which were virtually identical and displayed molecular ions at m/z 186, i.e. 100 mass units lower than the molecular mass of atROL. Even more surprising was the result of examining the high resolution mass spectra, suggestive of the presence of one sulfur atom in their molecules, analyzing for $C_9H_{14}O_2S$. Accurate mass measurements of the remaining major fragmentation ions in their mass spectra confirmed the presence of a sulfur atom in a majority of them. The intense peaks at m/z 155 ($M^+$ -$CH_2OH$) and 43 ($CH_3CO^+$) suggested a presence of hydroxymethyl and acetyl moieties. This conclusion was nicely confirmed by IR spectrum of Xa exhibiting bands at 3434 (OH) and 1713 (C=O) $cm^{-1}$. Mass spectra of acetyl and trimethylsilyl derivatives of metabolite Xa show molecular ions at m/z 228 and 258, respectively, as well as other fragment ions compatible with the presence of a derivatized primary hydroxyl group. The $^1H$ NMR spectrum of the major metabolite Xa showed two methyl signals at 1.788 and 2.17 ppm. The chemical shift of the latter was typical of an acetyl moiety in simple aliphatic acyclic ketones. The former singlet was slightly broadened and its chemical shift was characteristic of methyl groups connected to double bond systems. The presence of a double bond was confirmed by a signal at 5.48 ppm attributable to a vinyl proton. The NMR spectrum also displayed signals of six protons forming two ABX systems. The AB portion of the first system was centered at ca. 2.85 ppm and, as was shown by double resonance experiments, it was coupled to a methine proton resonating at 4.40 ppm. The signals of the protons belonging to the other AB part were centered at ca. 3.69 ppm and they were shown to be coupled to the other methine proton (4.19 ppm). Considering the chemical shifts and geminal coupling constants of the proton from both the AB parts and taking into account the fact that the deshielded methine protons, those corresponding to the respective X parts of the two ABX patterns concerned, are not coupled to each other, it was reasonable to assume that they belong to the $CH_3COCH_2$-CH and CH-$CH_2OH$ fragments which are, in turn, linked to a methyl-ethenylene group and a sulfide bridge.

The spectroscopic data of the minor metabolite Xb were found to be very similar to those of compound Xa. An interpretation of the NMR spectra of both compounds indicated that the only difference between them is the cis and trans orientation of substituents of the dihydrothiophene ring. 2-Hydroxymethyl-3-methyl-5-(2'-oxopropyl)-2,5-dihydrothiophene has two asymmetric carbons and can, therefore, exist in four isomeric forms. However, minute differences in the spectroscopic properties of the two metabolites and insufficient literature data (McIntosh & Messe, J. M., and Masse, G. M. Stereochemistry of dihydrothiophene formation from vinylphosphonium salts. J. Org. Chem. 40, 1294–1298, 1975) preclude the possibility of determination of their relative stereochemistry at C-11 and C-15. It is also unknown whether the metabolites are formed as single diastereomers, or they are a mixture of the corresponding optical antipodes.

The carbon skeleton of such 2,3,5-trisubstituted-2,5-dihydrothiophene compounds can be derived from atROL by an oxidative cleavage of its side chain C(8)–C(9) bond with the formation of a keto group at C-9. An incubation experiment using [15-$^3H$] atROL produced, after purification and separation on both RP-HPLC and NP-HPLC systems (data not shown), the same peaks with radioactivity as in the case of other $^3H$-labeled ([11, 12-$^3H$] or [20-$^3H$]) all-trans-retinols. This indicates the origin of the nine-carbon skeleton of metabolites and shows that the primary hydroxy group in the metabolites was derived from atROL.

The physiological importance of the involvement of sulfide in retinol metabolism remains to be determined. From protein, coenzymes, prothetic groups to the iron-sulfur clusters, sulfur is actively involved in many important redox processes (Voet and Voet, Biochemistry, John Wiley & Sons, New York, 1990). In mammalian tissues, sulfide can be released from desulfuration of cysteine by r-cystathionase and cysteine aminotransferase in conjunction with 3-mercaptopyruvate sulfurtransferase (Ogasawara et al, Biol. Pharm. Bull. 17, 1535–1542, 1994). Stipanuk, M. H. Annu. Rev. Nutr. 6, 179, 1986 postulated that the released sulfide was then incorporated into some pool of reduced sulfur that has a relatively long half-life prior to its oxidation.

Study by Ogasawara et al, Biol. Pharm. Bull. 17, 1535–1542, 1994 showed that bound sulfur was widely distributed in tissues and highest in kidneys. In kidneys, the bound sulfur was primarily located in the cytosolic fraction. In this study, the new retinol metabolite was produced by the cytosolic fraction of the VAD-RAS rat kidney cells. This indicates that the enzyme(s) that catalyze(s) the cleavage/oxidation and sulfide formation is/are located in the cytosolic fraction of the kidney cells.

During the last decade, the study of cytosolic sulfotransferases has been expanding. This family of enzymes catalyze the transfer of sulfur in sulfate form. Sulfonation has been reported in the metabolism of neurotransmitters, hormones, particularly steroid hormones and bile acids (Weinshilboum et al, In Conjugation-Deconjugation Reactions in Drug Metabolism and Toxicity (Kauffinan, F. C., ed), vol. 112, pp. 45–78, Springer-Verlag, Berlin Heidelberg, 1994; Weinshilboum, Federation Proc. 45, 2223–2228, 1986; Mulder et al, Conjugation Reactions in Drug Metabolism (Mulder, G. J., ed.) pp. 107–161, Taylor & Francis Ltd., New York, 1980; Falany, Trends Pharmacol. Sci. 12, 255–259, 1991). Some of the compounds can be bioactivated by sulfate incorporation. In contrast, this is the first time the involvement of sulfide in retinol metabolism has ever been reported. Our knowledge about sulfurtransferases and the characteristics of the reactions they catalyze is rather obscure. The metabolic route and structural identity of the other portion of the atROL molecule, i.e. the cyclohexane ring and the remainder of the side chain, are not known at the present time.

For treatment purposes, the novel compounds of this invention defined by the previous formula may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, topically, parenterally or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.01 μg to 100 μg per day, preferably from 0.1 μg to 50 μg per day, of the compounds are appropriate for treatment purposes, such doses being adjusted according to the disease to be treated, its severity and the response of the subject as is well understood in the art. The new compounds may be suitably administered alone, or together with graded doses of another pharmaceutically active compound in situations where a spectrum or different activities is found to be advantageous.

Compositions for use in the above-mentioned treatments comprise an effective amount of one or more metabolite(s) as defined by the above formula as the active ingredient, and a suitable carrier. An effective amount of such compounds for use in accordance with this invention is from about 0.01 μg to about 100 μg per gm of composition, and preferably from about 0.1 μg/gm to about 50 μg/gm of composition.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious of the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oil or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

The formulations may conveniently be presented in dosage unit form and may be prepared by any of the methods well known in the art of pharmacy. By the term "dosage unit" is meant a unitary, i.e. single dose which is capable of being administered to a patient as a physically and chemically stable unit dose comprising either the active ingredient as such or a mixture of it with solid or liquid pharmaceutical diluents or carriers.

We claim:

1. A compound having the formula:

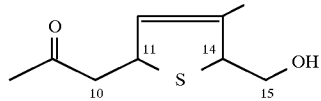

2. A pharmaceutical composition containing a compound having the formula

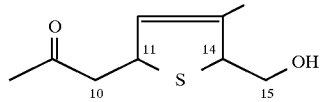

together with a pharmaceutically acceptable excipient.

* * * * *

UNITED STATES PATENT AND TRADEMARK OFFICE
CERTIFICATE OF CORRECTION

PATENT NO. : 5,880.292
DATED : March 9, 1999
INVENTOR(S) : Hector F. DeLuca et al It is certified that error appears in the above-indentified patent and that said Letters Patent is hereby corrected as shown below:

IN THE REFERENCES CITED:

Title Page    Under the title "U.S. Patent Documents" insert the following reference: ---Gander et al U.S. Patent No. 4,055,659---

Signed and Sealed this

Second Day of May, 2000

*Attest:*

Q. TODD DICKINSON

*Attesting Officer*    *Director of Patents and Trademarks*